United States Patent
Almirante et al.

(10) Patent No.: US 10,610,509 B2
(45) Date of Patent: Apr. 7, 2020

(54) COMBINATIONS OF PROSTAGLANDINS AND NITRIC OXIDE DONORS

(71) Applicant: NICOX S.A., Sophia Antipolis-Valbonne (FR)

(72) Inventors: Nicoletta Almirante, Milan (IT); Laura Storoni, Cesano Maderno (IT); Elena Bastia, Milan (IT); Francesco Impagnatiello, Milan (IT)

(73) Assignee: NICOX S.A., Valbonne (FR)

( * ) Notice: Subject to any disclaimer, the term of this patent is extended or adjusted under 35 U.S.C. 154(b) by 0 days.

(21) Appl. No.: 15/527,129

(22) PCT Filed: Nov. 17, 2015

(86) PCT No.: PCT/EP2015/076865
§ 371 (c)(1),
(2) Date: May 16, 2017

(87) PCT Pub. No.: WO2016/079142
PCT Pub. Date: May 26, 2016

(65) Prior Publication Data
US 2017/0354634 A1    Dec. 14, 2017

(30) Foreign Application Priority Data

Nov. 19, 2014  (EP) .................... 14193883

(51) Int. Cl.
| | | |
|---|---|---|
| A61K 31/34 | (2006.01) |
| A61K 31/343 | (2006.01) |
| A61K 31/164 | (2006.01) |
| A61K 31/191 | (2006.01) |
| A61K 9/00 | (2006.01) |
| A61K 31/5575 | (2006.01) |

(52) U.S. Cl.
CPC ............ *A61K 31/34* (2013.01); *A61K 9/0048* (2013.01); *A61K 31/164* (2013.01); *A61K 31/191* (2013.01); *A61K 31/343* (2013.01); *A61K 31/5575* (2013.01)

(58) Field of Classification Search
None
See application file for complete search history.

(56) References Cited

FOREIGN PATENT DOCUMENTS

| | | |
|---|---|---|
| EP | 1 386 611 A1 | 2/2004 |
| EP | 1386611 * | 2/2004 |
| EP | 2 238 143 B1 | 8/2012 |
| WO | 2009098113 * | 8/2009 |
| WO | WO 2014/063923 A1 | 5/2014 |

OTHER PUBLICATIONS

Impagnatiello et al., "A dual acting compound with latanoprost amide and nitric oxide releasing properties, show ocular hypotensive effects in rabbits and dogs," Experimental Eye Research, Feb. 15, 2011, pp. 243-249, vol. 93, No. 3, Academic Press Ltd. London.
International Search Report and Written Opinion issued in PCT/EP2015/076865 dated Feb. 4, 2016.
Rosenthal, R. et al., "Endothelin antagonism as an active principle for glaucoma therapy", British Journal of Pharmacology, 2011, vol. 162, No. 4, pp. 806-816.

* cited by examiner

*Primary Examiner* — Karl J Puttlitz
(74) *Attorney, Agent, or Firm* — Arent Fox, LLP

(57) ABSTRACT

The present invention relates to compositions for treating glaucoma and elevated ocular pressure. The compositions comprise a nitric oxide releasing isomannide derivative and a prostaglandin $F_{2\alpha}$ analog.

6 Claims, No Drawings

COMBINATIONS OF PROSTAGLANDINS AND NITRIC OXIDE DONORS

CROSS-REFERENCE TO RELATED APPLICATIONS

This application is a National Stage entry of International Application No.: PCT/EP2015/076865, filed Nov. 17, 2015, which claims priority to European Patent Application No. 14193883.7, filed Nov. 19, 2014. The disclosure of the priority applications are hereby incorporated in their entirety by reference.

The present invention relates to compositions comprising a Nitric oxide releasing isomannide derivative and a prostaglandin $F_{2\alpha}$ analog. More specifically, the invention discloses compositions for lowering intraocular pressure associated with glaucoma or with other ocular diseases.

Glaucoma, including hypertensive and normotensive glaucoma, is a disease of the eye characterized by a progressive loss of visual field due to irreversible damage to the optic nerve to the point where, if inadequately treated, glaucoma can lead to blindness or significant loss of vision.

Prior art treatment of glaucoma consists in lowering the intraocular pressure by administering drugs which either reduce the production of aqueous humor within the eye or increase the fluid drainage, such as beta adrenergic blockers, α-agonists, cholinergic agents, carbonic anhydrase inhibitors, and prostaglandin analogs.

Of these drugs, prostaglandin analogs facilitate aqueous humor from the uveoscleral outflow, thereby lowering intraocular pressure, and thus are commonly used in the treatment of glaucoma. However prostaglandin analogs such as, for example, bimatoprost, latanoprost, travoprost, tafluprost and unoprostone isopropyl, can produce ocular side effects, such as ocular irritation, conjunctival hyperaemia, iritis, uveitis, macular oedema, and increased pigmentation of the iris at therapeutically effective doses (Martindale, Thirty-third edition, p. 1445).

In the treatment of glaucoma and ocular hypertension, drugs having an intraocular pressure lowering action are used in combination to enhance the intraocular pressure lowering action. For example, EP 0 286 903 discloses the use of combinations of prostaglandin and a beta-adrenergic blocking agent US2013/0116254 discloses combination of the intraocular-lowering agents bimatoprost, brimonidine, and timolol.

Furthermore, WO 2013/060673, WO2014/170264 and WO2014/063923 disclose the use of quinone based nitric oxide donors alone and in combinations with prostaglandin analogs for treating glaucoma and intraocular pressure. The quinone based nitric oxide donors are disclosed for ophthalmic use. However, the patent applications do not provide evidence concerning the effects brought about by combining the quinone based nitric oxide donors with prostaglandin analogs.

EP 2 238 143B discloses nitric oxide releasing isohexide derivatives. The compounds have been disclosed for their use for treating cardiovascular diseases, hypertension, inflammation, pain, respiratory diseases, vascular diseases nephropathies and other pathological conditions including glaucoma and ocular hypertension. However, the patent does not provide evidence concerning the effects of the combination of a nitric oxide releasing isohexide derivatives and a prostaglandin analog.

U.S. Pat. No. 7,816,399 discloses the use of a mixture of latanoprost and a nitric oxide (NO) donor for treating or preventing ocular hypertension or glaucoma.

The patent discloses that combinations of latanoprost with nipradilol or sodium nitroprusside increase the ocular tension reducing effect when compared to the compounds used individually.

It has been unexpectedly found that the administration of nitric oxide releasing isomannide derivatives and prostaglandin $F_{2\alpha}$ analogs in combination exerts a greater reduction of intraocular pressure and a longer intraocular pressure decrease with respect to the same dose of either one of the two compounds given separately.

The synergic effect on the reduction of the intraocular pressure following co-administration of the nitric oxide releasing isomannide derivative and the prostaglandin $F_{2\alpha}$ analog will allow reducing the dosage of the prostaglandin $F_{2\alpha}$ analog thus decreasing or eliminating the side effects normally associated with the topical application of prostaglandin analogs.

Accordingly, these combinations are useful as therapeutic agents for treating glaucoma and ocular hypertension by lowering intraocular pressure.

Therefore, the present invention provides effective ophthalmic compositions for treating and/or preventing glaucoma and ocular hypertension having reduced side effects and, thereby, enhanced patient compliance.

The present invention relates to compositions comprising
(i) a nitric oxide releasing isomannide derivative of the following formula (I) or a stereoisomer thereof:

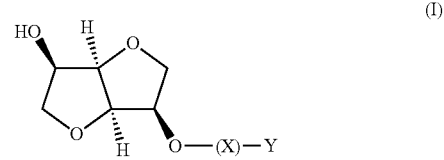

(I)

X is —CO— or —COO—;

Y is straight or branched $C_1$-$C_{10}$ alkyl chain, substituted with one or two —$ONO_2$; or $C_1$-$C_6$ alkylenoxy-$C_1$-$C_5$ alkyl wherein the alkyl group is substituted by one or two —$ONO_2$ groups.

(ii) a prostaglandin $F_{2\alpha}$ analog selected from the group consisting of latanoprost, bimatoprost, travoprost, tafluprost or unoprostone isopropyl, preferably the prostaglandin $F_{2\alpha}$ analog is travoprost or bimatoprost.

A preferred embodiment of the invention provides compositions comprising:

(i) a nitric oxide releasing isomannide derivative of formula (I) that is selected from the group:

(3R,3aR,6R,6aR)-6-hydroxyhexahydrofuro[3,2-b]furan-3-yl 4-(nitrooxy) butanoate (Compound (1))

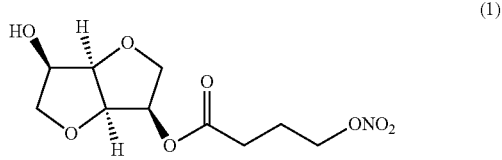

(1)

(3R,3aR,6R,6aR)-6-hydroxyhexahydrofuro[3,2-b]furan-3-yl 6-(nitrooxy) hexanoate (Compound (2))

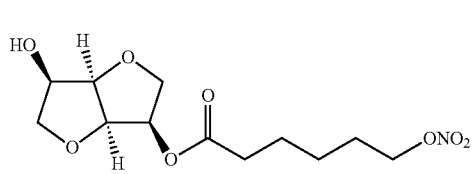

(2)

(3R,3aR,6R,6aR)-6-hydroxyhexahydrofuro[3,2-b]furan-3-yl 5,6-bis (nitrooxy) hexanoate (Compound (3))

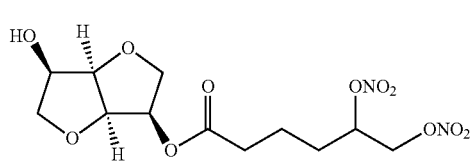

(3)

(3R,3aR,6R,6aR)-6-hydroxyhexahydrofuro[3,2-b]furan-3-yl 3-(2,3-bis(nitrooxy)propoxy)propanoate (Compound (4))

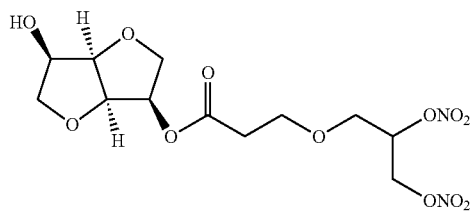

(4)

(3R,3aR,6R,6aR)-6-hydroxyhexahydrofuro[3,2-b]furan-3-yl 4,5-bis (nitrooxy)hexanoate (Compound (5))

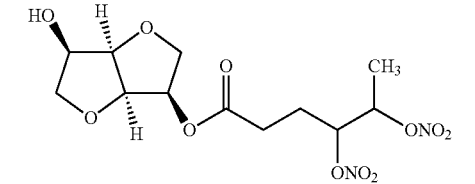

(5)

(3R,3aR,6R,6aR)-6-hydroxyhexahydrofuro[3,2-b]furan-3-yl 4-(nitrooxy) butyl carbonate (Compound (6))

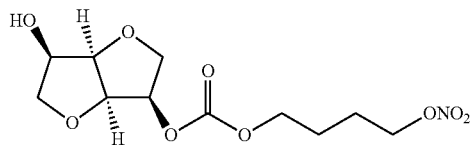

(6)

4,5-bis(nitrooxy)hexyl (3R,3aR,6R,6aR)-6-hydroxyhexahydrofuro[3,2-b]furan-3-yl carbonate (Compound (7))

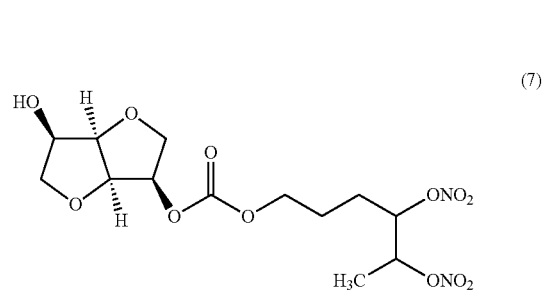

(7)

5,6-bis(nitrooxy)hexyl (3R,3aR,6R,6aR)-6-hydroxyhexahydrofuro[3,2-b]furan-3-yl carbonate (Compound (8))

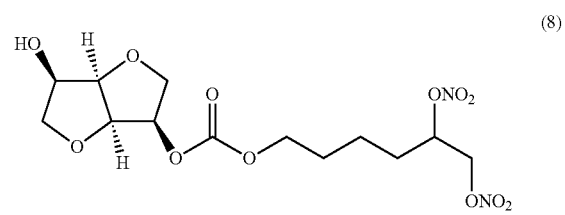

(8)

2-(2,3-bis(nitrooxy)propoxy)ethyl(3R,3aR,6R,6aR)-6-hydroxyhexahydrofuro[3,2-b]furan-3-yl carbonate (Compound (9))

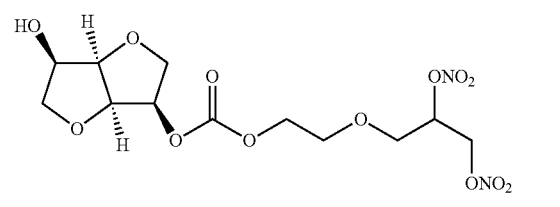

(9)

3,3-dimethyl-5,6-bis(nitrooxy)hexyl (3R,3aR,6R,6aR)-6-hydroxyhexahydrofuro[3,2-b]furan-3-yl carbonate (Compound (10))

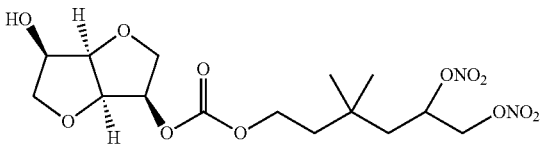

(10)

(3R,3aR,6R,6aR)-6-hydroxyhexahydrofuro[3,2-b]furan-3-yl 6-(nitrooxy) hexyl carbonate (Compound (11))

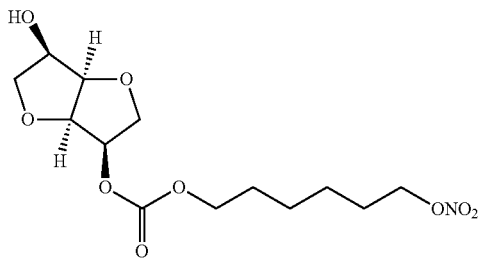

(S)-((3R,3aR,6R,6aR)-6-hydroxyhexahydrofuro[3,2-b]furan-3-yl) 5,6-bis(nitrooxy)hexanoate (Compound (12))

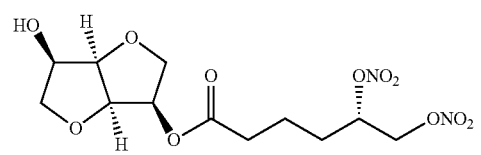

and stereoisomer thereof (ii) a prostaglandin $F_{2\alpha}$ analog selected from the group consisting of: latanoprost, bimatoprost, travoprost, tafluprost and unoprostone isopropyl.

Another embodiment of the invention provides compositions comprising:

(i) a nitric oxide releasing isomannide derivative of formula (I) that is selected from the group:

(3R,3aR,6R,6aR)-6-hydroxyhexahydrofuro[3,2-b]furan-3-yl 4-(nitrooxy) butanoate (Compound (1))

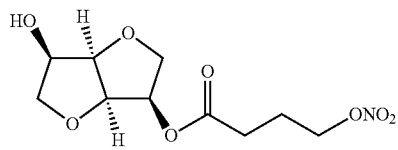

(3R,3aR,6R,6aR)-6-hydroxyhexahydrofuro[3,2-b]furan-3-yl 6-(nitrooxy) hexanoate (Compound (2))

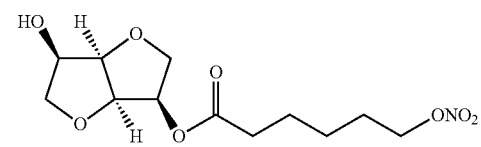

(3R,3aR,6R,6aR)-6-hydroxyhexahydrofuro[3,2-b]furan-3-yl 5,6-bis (nitrooxy) hexanoate (Compound (3))

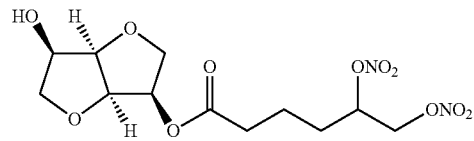

(3R,3aR,6R,6aR)-6-hydroxyhexahydrofuro[3,2-b]furan-3-yl 3-(2,3-bis(nitrooxy)propoxy)propanoate (Compound (4))

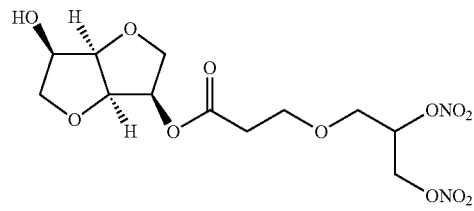

(3R,3aR,6R,6aR)-6-hydroxyhexahydrofuro[3,2-b]furan-3-yl 4,5-bis (nitrooxy)hexanoate (Compound (5))

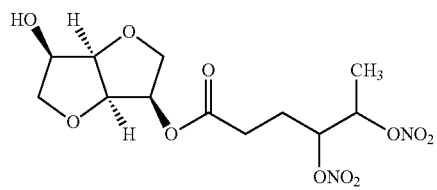

(3R,3aR,6R,6aR)-6-hydroxyhexahydrofuro[3,2-b]furan-3-yl 4-(nitrooxy) butyl carbonate (Compound (6))

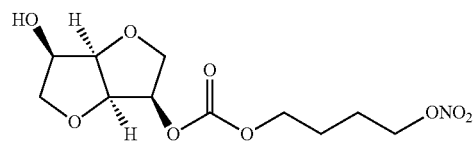

4,5-bis(nitrooxy)hexyl (3R,3aR,6R,6aR)-6-hydroxyhexahydrofuro[3,2-b]furan-3-yl carbonate (Compound (7))

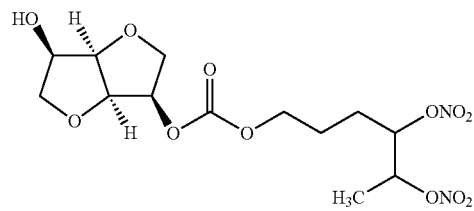

5,6-bis(nitrooxy)hexyl (3R,3aR,6R,6aR)-6-hydroxyhexahydrofuro[3,2-b]furan-3-yl carbonate (Compound (8))

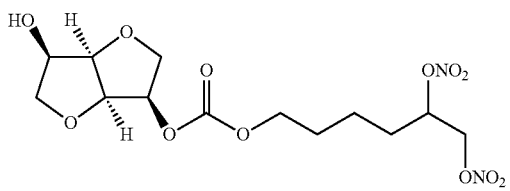

2-(2,3-bis(nitrooxy)propoxy)ethyl(3R,3aR,6R,6aR)-6-hydroxyhexahydrofuro[3,2-b]furan-3-yl carbonate (Compound (9))

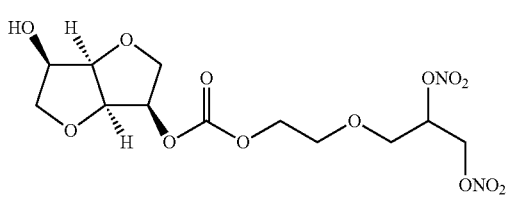

3,3-dimethyl-5,6-bis(nitrooxy)hexyl (3R,3aR,6R,6aR)-6-hydroxyhexahydrofuro[3,2-b]furan-3-yl carbonate (Compound (10))

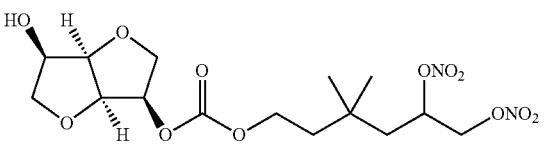

(3R,3aR,6R,6aR)-6-hydroxyhexahydrofuro[3,2-b]furan-3-yl 6-(nitrooxy) hexyl carbonate (Compound (11))

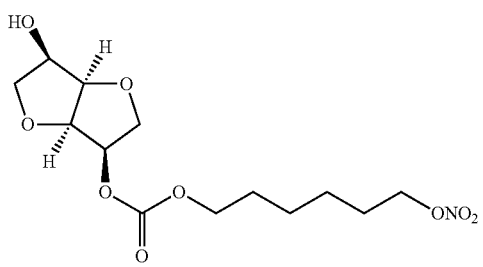

(S)-((3R,3aR,6R,6aR)-6-hydroxyhexahydrofuro[3,2-b]furan-3-yl) 5,6-bis(nitrooxy)hexanoate (Compound (12))

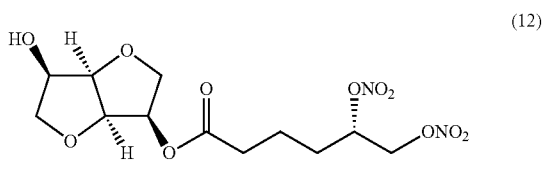

and stereoisomer thereof (ii) a prostaglandin $F_{2\alpha}$ analog that is travoprost or bimatoprost.

Another embodiment of the invention provides compositions comprising:

(i) a nitric oxide releasing isomannide derivative of formula (I) that is (S)-((3R,3aR,6R,6aR)-6-hydroxyhexahydrofuro[3,2-b]furan-3-yl) 5,6-bis(nitrooxy)hexanoate (Compound (12))

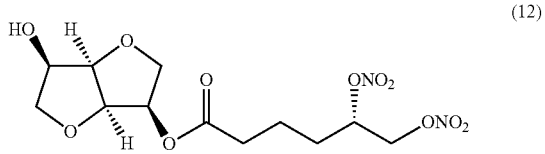

and (ii) a prostaglandin $F_{2\alpha}$ analog that selected from the group consisting of latanoprost, bimatoprost, travoprost, tafluprost and unoprostone isopropyl.

Another embodiment of the invention provides compositions comprising:

(ii) a nitric oxide releasing isomannide derivative of formula (I) that is (S)-((3R,3aR,6R,6aR)-6-hydroxyhexahydrofuro[3,2-b]furan-3-yl) 5,6-bis(nitrooxy)hexanoate (Compound (12))

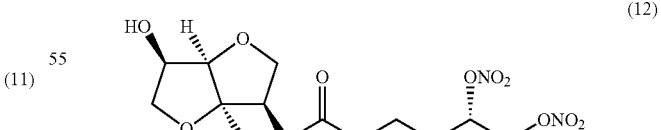

and (ii) a prostaglandin $F_{2\alpha}$ analog that is travoprost.

Another embodiment of the invention provides compositions comprising:

(i) a nitric oxide releasing isomannide derivative of formula (I) that is (S)-((3R,3aR,6R,6aR)-6-hydroxyhexahydrofuro[3,2-b]furan-3-yl) 5,6-bis(nitrooxy)hexanoate (Compound (12))

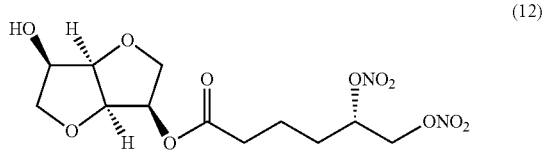

(12)

and (ii) a prostaglandin $F_{2\alpha}$ analog selected that is bimatoprost.

The weight ratio of the nitric oxide releasing isomannide derivative of formula (I) to the prostaglandin $F_{2\alpha}$ analog is generally 1:1 to 10000:1 and preferably is 5:1 to 1000:1.

The present invention also provides compositions comprising a nitric oxide releasing isomannide derivative of formula (I) and a prostaglandin $F_{2\alpha}$ analog as above defined, for the treatment of glaucoma, ocular hypertension and for reducing intraocular pressure associated with ocular diseases.

Another embodiment of the present invention provides ophthalmic pharmaceutical formulation comprising at least a nitric oxide releasing isomannide derivative of formula (I) as defined above, a prostaglandin $F_{2\alpha}$ analog and at least an ophthalmic excipient.

The ophthalmic excipients may include for example, buffers, tonicity agents, chelating agents, viscosity enhancers, solubilizing agents, surfactants, antioxidants, preservatives or ophthalmic vehicles.

The ophthalmic pharmaceutical formulation of the present invention can be in the form of solutions, suspensions, emulsions, dispersions, topical eye drops, or gel tears.

In general, ophthalmic pharmaceutical formulation of the present invention will include the compounds of formula (I) in an amount between about 0.001 and about 10% percent by weight (w/v %) and the prostaglandin $F_{2\alpha}$ analog in an amount between about 0.0001 and about 0.2 w/v %.

It is preferred to use nitric oxide releasing isomannide derivatives of formula (I) in an amount between about 0.005 and about 2.0 w/v %, and it is especially preferred to use an amount between about 0.01 and about 0.5 w/v %. It is preferred to use the prostaglandin $F_{2\alpha}$ analog in an amount between about 0.0001 and about 0.1 w/v %, depending on the potency of the prostaglandin.

A combination of a nitric oxide releasing isomannide derivative of formula (I) and a prostaglandin $F_{2\alpha}$ analog according to the present invention may be prepared in one dosage form comprising effective amounts of the respective compounds at a suitable mixing ratio or as a kit used by administering each preparation comprising an effective amount of each compound simultaneously or separately at an interval.

The nitric oxide releasing isomannide derivatives of formula (I) are described in EP 2 238 143B; this patent discloses structures, preparations and physical properties of these compounds.

The prostaglandin $F_{2\alpha}$ analogs used in the compositions of the invention have been known as agents for treatment of glaucoma and they are:

latanoprost is 5-heptenoic acid, 7-[(1R,2R,3R,5S)-3,5-dihydroxy-2-[(3R)-3-hydroxy-5-phenylpentyl]cyclopentyl]-, 1-methylethyl ester, (5Z)-;

bimatoprost is 5-heptenamide, 7-[(1R,2R,3R,5S)-3,5-dihydroxy-2-[(1E,3S)-3-hydroxy-5-phenyl-1-penten-1-yl]cyclopentyl]-N-ethyl-, (5Z)-;

travoprost is 5-heptenoic acid, 7-[(1R,2R,3R,5S)-3,5-dihydroxy-2-[(1E,3R)-3-hydroxy-4-[3-(trifluoromethyl)phenoxy]-1-buten-1-yl]cyclopentyl]-, 1-methylethyl ester, (5Z)-;

tafluprost is 5-heptenoic acid, 7-[(1R,2R,3R,5S)-2-[(1E)-3,3-difluoro-4-phenoxy-1-buten-1-yl]-3,5-dihydroxycyclopentyl]-, 1-methylethyl ester, (5Z)-;

unoprostone isopropyl is 5-heptenoic acid, 7-[(1R,2R,3R,5S)-3,5-dihydroxy-2-(3-oxodecyl)cyclopentyl]-, 1-methylethyl ester, (5Z)-.

Latanoprost, bimatoprost, travoprost, tafluprost or unoprostone isopropyl are commercially available.

EXAMPLES

Example 1

Intraocular Pressure (IOP) Lowering Activity in Ocular Normotensive New Zealand White (NZW) Rabbits The Intraocular pressure (IOP) lowering activity of the combination of compound (12) (0.1%) and travoprost (0.004%) was assessed in ocular normotensive rabbits.

Adults male NZW rabbits weighting 1.8-2.0 Kg were used in the experiments.

IOP was measured using a pneumatonometer 30 CLASSIC™ before topical application (basal) and at different time points (30, 60, 120, 180, 240 and 300 min) thereafter. Travoprost (0.004%) or vehicle (5% cremophor-EL; 0.3% DMSO; 0.2 mg/ml BAC in PBS pH 6.0) were topically administered 5 minutes prior to compound (12) (0.1%) or vehicle (same as above) as eye drops into the conjunctiva pocket. Eyes were randomly assigned to different treatment groups. One drop of 0.4% oxybuprocaine hydrochloride (Novesine, Sandoz) was instilled in each eye immediately before each set of ocular pressure measurements.

Results are reported in the table in which the ocular hypotensive activity of the combination, of compound (12) and of travoprost are expressed as IOP change (at 30, 60, 120 and 300 minutes following topical administration) versus vehicle and versus IOP at basal (mean±standard error).

The combination of compound (12) (0.1%) and travoprost (0.004%) results in increased IOP lowering activity compared to either compound (12) (0.1%) or travoprost (0.004%) given alone. Moreover, the effects of the combination last significantly longer than either compound (12) (0.1%) alone or travoprost (0.004%) alone.

The above mentioned results revealed that an enhanced intraocular pressure lowering effect and improvement of the duration of intraocular pressure lowering action could be obtained by using a nitric oxide releasing isomannide derivative of formula (I) and a prostaglandin $F_{2\alpha}$ analog in combination. The intraocular pressure lowering effect is greater than simple additivity, especially at the longer durations.

TABLE 1

Intraocular pressure (IOP) lowering activity
in ocular normotensive NZW rabbits

| | IOP change (mmHg) | | | | |
|---|---|---|---|---|---|
| | 30 minutes | 60 minutes | 120 minutes | 180 minutes | 300 minutes |
| Compound (12) | −1.4 ± 0.6 | −2.1 ± 0.4 | −0.3 ± 0.3 | 0.1 ± 0.5 | 1.1 ± 0.8 |
| Travoprost | −1.6 ± 1.6 | −0.9 ± 1.0 | −1.1 ± 1.2 | −0.8 ± 0.4 | −0.6 ± 0.1 |
| Compound (12) + Travoprost | −3.9 ± 0.8 | −2.6 ± 0.9 | −3.2 ± 0.6 | −3.4 ± 0.5 | −2.6 ± 0.7 |

Example 2

Intraocular Pressure (IOP) Lowering Activity in Ocular Hypertensive New Zealand White (NZW) Rabbits The Intraocular pressure (IOP) lowering activity of the combination of compound (12) (0.3%) and travoprost (0.004%) was assessed in ocular hypertensive rabbits.

Adult male NZW rabbits weighting 1.8-2.0 Kg were used in the experiments.

NZW rabbits were injected with 0.1 ml of hypertonic saline (5%) into the vitreous humor of both eyes. IOP was measured using a Tono-Pen AVIA Vet® at different time points (30, 60, 120 and 240 min) following hypertonic saline injection as well as before topical drug application (basal).

Travoprost (0.004%) or vehicle (5% cremophor-EL; 0.3% DMSO; 0.2 mg/ml BAC in PBS pH 6.0) were topically administered 15 min before hypertonic saline injection.

Compound (12) (0.3%) or vehicle (5% cremophor-EL; 0.3% DMSO; 0.2 mg/ml BAC in PBS pH 6.0) were topically administered immediately after hypertonic saline injection. Eyes were randomly assigned to different treatment groups.

One drop of 0.4% oxybuprocaine hydrochloride (Novesine, Sandoz) was instilled in each eye immediately before each set of ocular pressure measurements.

The ocular hypotensive effects (at 30, 60, 120 and 300 minutes following topical administration) of travoprost, compound (12) and the combination of compound (12) and travoprost are reported in table 2.

The results reported in table 2 are expressed as IOP change (at 30, 60, 120 and 300 minutes following topical administration) versus vehicle and versus IOP at basal (mean±standard error).

The results show that the combination of compound (12) and travoprost has an increased IOP lowering activity compared to either compound (12) or travoprost given alone and that the combination of compound (12) and travoprost induces an enhanced and sustained intraocular pressure lowering effect at longer time points.

TABLE 2

Intraocular pressure (IOP) lowering activity in ocular hypertensive NZW rabbits

| | IOP change (mmHg) | | | |
|---|---|---|---|---|
| | 30 minutes | 60 minutes | 120 minutes | 240 minutes |
| Travoprost | −2.4 ± 0.5 | −5.0 ± 0.8 | −5.1 ± 0.7 | −1.7 ± 0.4 |
| Compound (12) | −2.4 ± 0.6 | −7.7 ± 0.5 | −6.4 ± 0.5 | −1.8 ± 0.6 |
| Compound (12) + travoprost | −2.5 ± 0.8 | −9.6 ± 1.0 | −9.6 ± 0.8 | −3.2 ± 0.7 |

The invention claimed is:

1. A composition comprising:
   (i) a nitric oxide releasing isomannide derivative of formula (I) that is (S)-((3R,3aR,6R,6aR)-6-hydroxyhexahydrofuro[3,2-1D]furan-3-yl)5,6-bis(nitrooxy)hexanoate (Compound (12)), and,
   (ii) a prostaglandin F2α analog selected from the group consisting of latanoprost.

2. The compositions according to claim 1 wherein the weight ratio of the nitric oxide releasing isomannide derivative of formula (I) to the prostaglandin F2α analog is 1:1 to 10000:1.

3. Ophthalmic pharmaceutical formulations comprising a composition according to claim 1 and at least one ophthalmic excipient.

4. A kit comprising: a nitric oxide releasing isomannide derivative of formula (I) according to claim 1 and a prostaglandin F2α analog according to claim 1 for administering the compounds simultaneously or separately at an interval.

5. A composition according to claim 1, wherein the prostaglandin F2α analog is latanoprost.

6. A composition according to claim 1, wherein the composition comprises the nitric oxide releasing isomannide derivative of formula (I) and the prostaglandin F2α analog in an amount effective to reduce ocular tension in a subject at 180 minutes after administration.

* * * * *